(12) United States Patent
Law

(10) Patent No.: US 8,784,453 B1
(45) Date of Patent: Jul. 22, 2014

(54) DYNAMIC SPINAL STABILIZATION SYSTEM

(71) Applicant: Melvin Law, Brentwood, TN (US)

(72) Inventor: Melvin Law, Brentwood, TN (US)

( * ) Notice: Subject to any disclaimer, the term of this patent is extended or adjusted under 35 U.S.C. 154(b) by 0 days.

(21) Appl. No.: 13/718,225

(22) Filed: Dec. 18, 2012

Related U.S. Application Data

(63) Continuation-in-part of application No. 13/233,442, filed on Sep. 15, 2011, which is a continuation of application No. 12/480,085, filed on Jun. 8, 2009, now Pat. No. 8,043,340.

(60) Provisional application No. 61/059,899, filed on Jun. 9, 2008.

(51) Int. Cl.
*A61B 17/70* (2006.01)

(52) U.S. Cl.
USPC .......................................................... 606/257

(58) Field of Classification Search
USPC ................................................. 606/246–279
See application file for complete search history.

(56) References Cited

U.S. PATENT DOCUMENTS

| | | | |
|---|---|---|---|
| 5,413,602 | A | 5/1995 | Metz-Stavenhagen |
| 5,672,175 | A | 9/1997 | Martin |
| 7,326,210 | B2 | 2/2008 | Jahng et al. |
| 7,699,875 | B2 | 4/2010 | Timm |
| 7,927,356 | B2 | 4/2011 | Lim |
| 8,043,340 | B1 | 10/2011 | Law |
| 8,535,351 | B1 | 9/2013 | Law |
| 2002/0095154 | A1 | 7/2002 | Atkinson et al. |
| 2003/0220643 | A1 | 11/2003 | Ferree |
| 2004/0143264 | A1 | 7/2004 | McAfee |
| 2005/0143737 | A1 | 6/2005 | Pafford et al. |
| 2005/0177156 | A1 | 8/2005 | Timm et al. |
| 2005/0203519 | A1 | 9/2005 | Harms et al. |
| 2006/0036240 | A1 | 2/2006 | Colleran et al. |
| 2006/0229613 | A1 | 10/2006 | Timm et al. |
| 2006/0247635 | A1 | 11/2006 | Gordon et al. |
| 2006/0264937 | A1 | 11/2006 | White |
| 2006/0264940 | A1 | 11/2006 | Hartmann |
| 2007/0233085 | A1 | 10/2007 | Biedermann et al. |
| 2007/0288012 | A1 | 12/2007 | Colleran et al. |
| 2007/0293862 | A1 | 12/2007 | Jackson |
| 2008/0140076 | A1 | 6/2008 | Jackson |
| 2008/0147122 | A1 | 6/2008 | Jackson |
| 2008/0183213 | A1 | 7/2008 | Veldman et al. |
| 2008/0195153 | A1 | 8/2008 | Thompson |
| 2008/0300633 | A1 | 12/2008 | Jackson |
| 2009/0093846 | A1 | 4/2009 | Hestad |
| 2009/0099606 | A1 | 4/2009 | Hestad et al. |
| 2009/0216274 | A1 | 8/2009 | Morancy-Meister et al. |
| 2009/0259258 | A1 | 10/2009 | Perez-Cruet et al. |
| 2009/0275985 | A1 | 11/2009 | Jackson |
| 2009/0326584 | A1 | 12/2009 | Slivka et al. |
| 2010/0087862 | A1 | 4/2010 | Biedermann et al. |
| 2010/0087865 | A1 | 4/2010 | Biedermann et al. |
| 2010/0174319 | A1 | 7/2010 | Jackson |
| 2011/0029022 | A1 | 2/2011 | Zehnder et al. |
| 2011/0082504 | A1 | 4/2011 | Singhatat et al. |
| 2012/0035660 | A1 | 2/2012 | Jackson |
| 2012/0041493 | A1 | 2/2012 | Miller et al. |

*Primary Examiner* — Pedro Philogene
*Assistant Examiner* — David Comstock
(74) *Attorney, Agent, or Firm* — Luedeka Neely Group, P.C.; Robert O. Fox

(57) ABSTRACT

A dynamic spinal stabilization system that enables spinal movements throughout a range of motions from a neutral condition of the spine, to a flexion condition, and an extension condition. The system includes elastomeric members operatively located to substantially eliminate metal-to-metal contact of metal components of the system that are movable relative to one another, one of the elastomeric members having a stepped configuration.

4 Claims, 5 Drawing Sheets

DYNAMIC SPINAL STABILIZATION SYSTEM

CROSS-REFERENCE TO RELATED APPLICATION

This application is a continuation-in-part of co-pending U.S. application Ser. No. 13/233,442 filed Sep. 15, 2011, and entitled "Dynamic Spinal Stabilization System," which is a continuation of U.S. application Ser. No. 12/480,085 filed Jun. 8, 2009, and entitled "Dynamic Spinal Stabilization System (now U.S. Pat. No. 8,043,340 issued Oct. 25, 2011), which claims priority to U.S. Provisional Application Ser. No. 61/059,899 filed Jun. 9, 2008, and entitled "Spine Stabilizer," incorporated by reference herein in its entirety.

FIELD

This disclosure relates to the field of dynamic spinal stabilization devices. More particularly, this disclosure relates to dynamic spinal stabilization devices that utilize metal components, but which avoid metal-to-metal contact associated with relative movement of components.

BACKGROUND

While there are a variety of causes of spinal pain, in many instances such pain results from mis-alignment of members of the spine and/or changes in spacing of members of the spine. Often, these conditions result from degeneration, either from age or injury, of spinal discs. The primary surgical treatment options for disc degeneration are spinal fusion and dynamic stabilization.

Spinal fusion is a surgical procedure in which degenerated discs are removed and the resulting adjacent discs are held together by use of a rigid system of pedicle screws and rods until the discs grow together and fuse.

Dynamic stabilization is a surgical procedure that avoids disc removal and utilizes an elastomeric implant that restores desired alignment and spacing of vertebrae, relieves weight overload of individual discs, and permits substantially normal spinal movements. Improvement is desired in the provision of dynamic spinal stabilizers.

Spinal implants typically utilize various metal components, such as pedicle screws and rods. One problem associated with conventional dynamic stabilization devices is metal-to-metal contact of the various components, such as contact between the metal rod and the metal screw. Such metal-to-metal contact is undesirable, as metal-to-metal contact can result in metal flakes which flakes can be inflammatory and painful to the patient, and compromise the structural integrity of the stablizer.

Another disadvantage of conventional stabilizers is the presence of gaps between components of the stabilizer. Gaps are undesirable, as tissue can grow into gaps and interfere with the operation of the stabilizer and cause pain to the patient.

The present disclosure advantageously provides improved dynamic stabilization systems that avoid metal-to-metal contact of components that move relative to one another and minimize undesirable gaps between components of the system.

SUMMARY

The above and other needs are met by dynamic stabilization systems that enable spinal movements throughout a range of motions from a neutral condition of the spine, to a flexion condition, and an extension condition.

The systems include metal pedicle screws and at least one metal support rod, with elastomeric members operatively located to substantially eliminate metal-to-metal contact of metal components of the system that are movable relative to one another, and to minimize gaps between components of the system.

In one aspect, a dynamic system is provided that includes a first metal pedicle screw and a second metal pedicle screw each installable in a vertebrae; a metal support rod; a first metal connector mountable to the first pedicle screw and fixedly disposed on the rod; a second metal connector mountable to the second pedicle screw and slidingly disposed on the rod at a location spaced apart from the first connector; and a rigid metal member fixed to the rod and spaced apart from a side of the second connector opposite the first connector.

A first elastomeric sleeve is positioned on the rod and located between the first and second connectors, the first elastomeric sleeve having a stepped configuration and including a first section and a second section having a smaller exterior dimension than the corresponding dimension of the first section and sized to fit within a portion of the second connector so as to be situated between the second metal connector and the rod to substantially eliminate metal-to-metal contact between the second metal connector and the rod. A second elastomeric sleeve is located between the second connector and the rigid member.

The sleeves are operative to substantially eliminate contact between the metal rod and the first and second metal connectors so as to substantially eliminate metal-to-metal contact of metal components of the system that are movable relative to one another. The sleeves deform to enable spinal movements throughout a range of motions from a neutral condition of the spine, to a flexion condition, and an extension condition.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

With reference to the drawings, the disclosure relates to dynamic stabilization systems that avoid metal-to-metal contact of components that move relative to one another and minimize undesirable gaps between components of the system. The systems described herein are particularly configured for use in stabilizing lumbar regions of the human spine, and are also suitable for use to stabilize the thoracic region.

Figure 1:
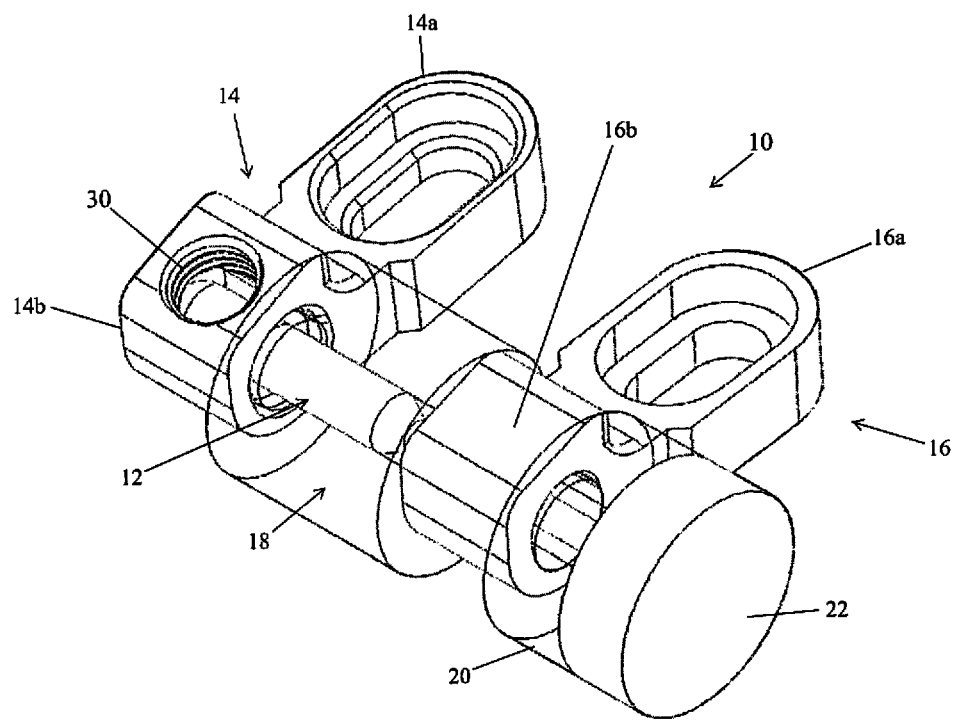
FIG. 1 is a perspective view of a dynamic stabilization system according to the disclosure.
Figure 2:
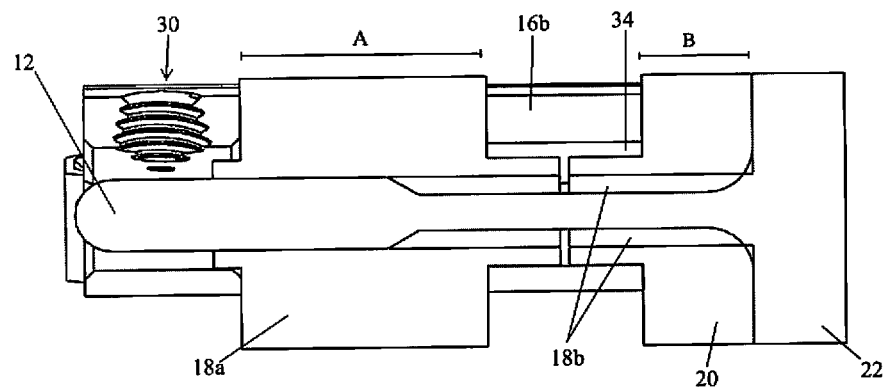
FIG. 2 is a cross-sectional side view of the stabilization system of FIG. 1.

With reference to FIGS. 1 and 2, there is shown a dynamic stabilization system 10 configured to be mounted in an off-set relationship to a pair of pedicle screws or other structure fixed relative to a spine.

The system 10 includes a rigid support rod 12, a fixed connector 14, a sliding connector 16, a step cut elastomeric sleeve 18, a washer shaped elastomeric sleeve 20, and a fixed rigid member 22.

The system 10 is configured so that the connectors 14 and 16 are offset from and connect to a pair of pedicle screws or other structure fixed relative to a spine. The support rod 12 is an elongate rod made of a biocompatible material suitable for implanting in the human body, such as biocompatible metals including titanium and alloys thereof, and of suitable dimensions for spinal stabilization purposes. The rod 12 is preferably of circular cross-section and preferably substantially straight, but, if desired may be bent or curved, such as to impart lordosis or inward curvature to the adjacent portion of the spine.

The connectors 14 and 16 and the rigid member 22 are also made of a biocompatible material suitable for implanting in the human body, such as biocompatible metals including titanium and alloys thereof, and of suitable dimensions for spinal stabilization purposes. The materials of these components are selected so as to be compatible with one another, including electrical compatibility to avoid electrolysis, and are generally made of the same materials.

The fixed connector 14 has a mount 14a configured to mount to a pedicle screw or like structure fixed to the spine. A receiver 14b is located opposite the mount 14a and is configured for receiving the support rod 12. A threaded aperture 30 extends through a sidewall of the receiver 14b to receive a set screw or the like securement structure for fixedly securing the connector 14 to the support rod 12 so that the support rod 12 does not move relative to the connector 14 once the system 10 is installed.

The sliding connector 16 has a mount 16a configured to mount to a pedicle screw or like structure fixed to the spine. A receiver 16b is located opposite the mount 16a and is configured for receiving the support rod 12. The connector 16 is not fixed to the connecting rod 12 and may move relative to the connecting rod 12.

Figure 3:
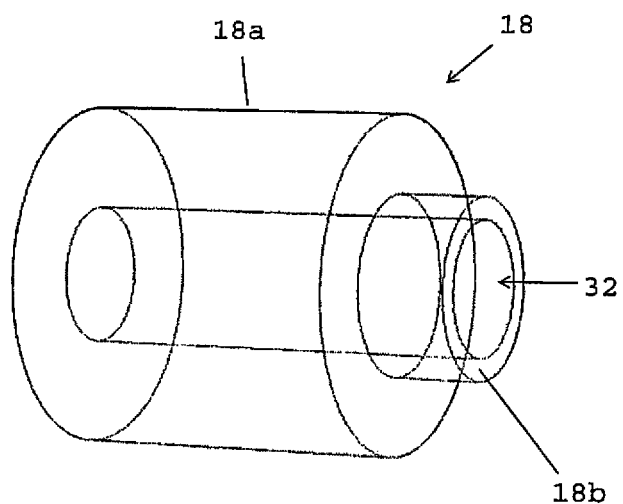
FIG. 3 is a perspective view of a step cut elastomeric sleeve component of the disclosed system.

With additional reference to FIG. 3, the step cut elastomeric sleeve 18 is of one-piece construction and made of a biocompatible elastomeric material such as silicone, polycarbonate urethane, and other biocompatible thermoplastic elastomers. The sleeve 18 has a general cylindrical shape and defines an internal bore 32 corresponding to the diameter or dimension of the support rod 12. The sleeve 18 is step cut to provide a first cylindrical section 18a and a second cylindrical section 18b having a smaller exterior diameter or dimension than the diameter or dimension of the first section 18a. The first section 18a has an exterior dimension configured to be larger than the exterior dimensions of the portions of the receivers 14b and 16b of the receivers 14 and 16. The second section 18b is sized to fit within a through a bore 34 of the receiver 16b. The first cylindrical section 18a of the sleeve 18 has a length sufficient to substantially bridge a gap distance A defined between the connectors 14 and 16 when the system 10 is in a neutral environment corresponding to the spine on which the system 10 is installed. The second cylindrical section 18b has a length corresponding to the length of the bore 34 of the receiver 16b.

Figure 4:
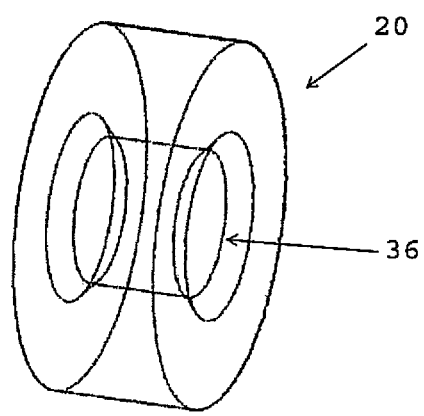
FIG. 4 is a perspective view of a washer-shaped elastomeric sleeve component of the disclosed system.

With reference to FIG. 4, the washer shaped elastomeric sleeve 20 is of one-piece construction and made of a biocompatible elastomeric material such as silicone, polycarbonate urethane, and other biocompatible thermoplastic elastomers. The sleeve 20 has a general cylindrical shape and defines an internal bore 36 corresponding to the diameter or dimension of the support rod 12. The sleeve 20 has a length sufficient to substantially bridge a gap distance B defined between the connector 16 and the rigid member 22 when the system 10 is in a neutral environment corresponding to the spine on which the system 10 is installed. The ends of the bore 36 may be flared so as to reduce the likelihood of suction forces occurring due to movement of the sliding connector 16.

The rigid member 22 may be part of the rod 12, such as a head of the rod 12, or may be a separate member that is fixed to the rod as by use of a set screw or the like.

Figure 5A:
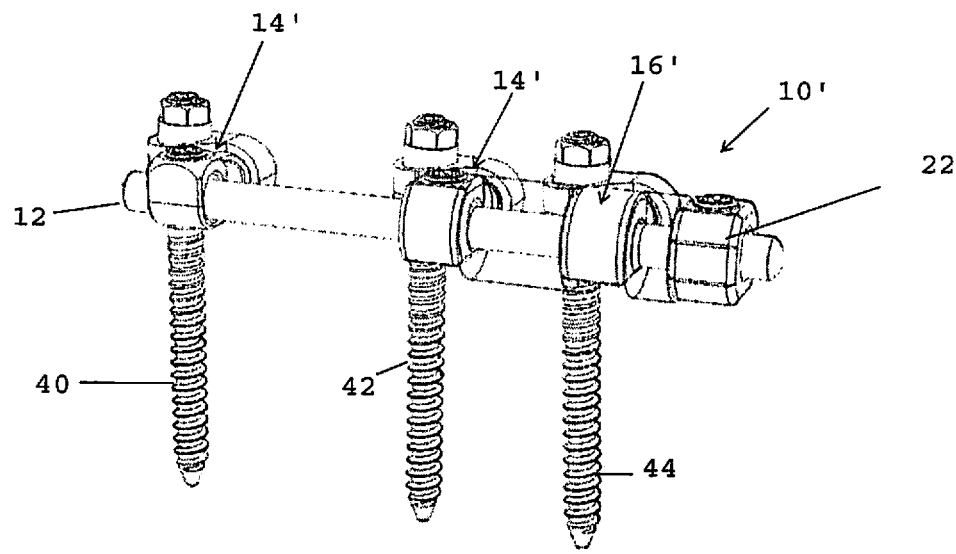
FIG. 5A is a front perspective view of a stabilization system according to the disclosure shown with pedicle screws.
Figure 5B:
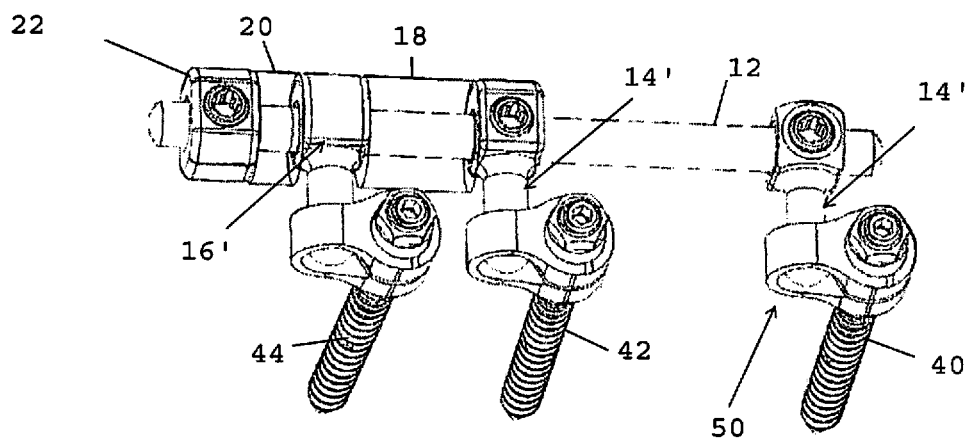
FIG. 5B is a rear perspective view thereof.
Figure 5C:
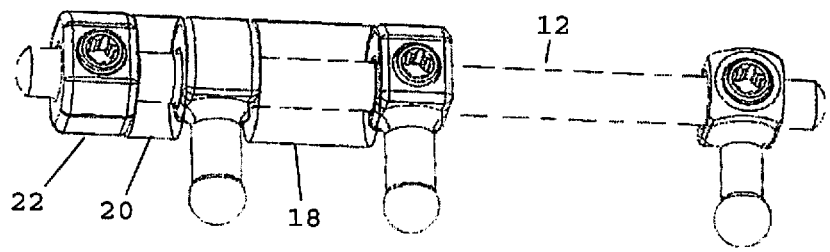
FIG. 5C is a rear perspective view with the pedicle screws absent.
Figure 6A:
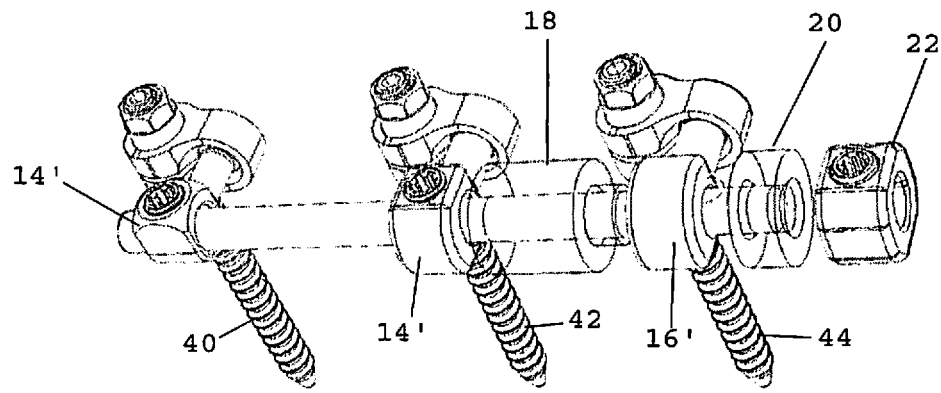
FIG. 6A is a partially exploded view of FIG. 5A.
Figure 6B:
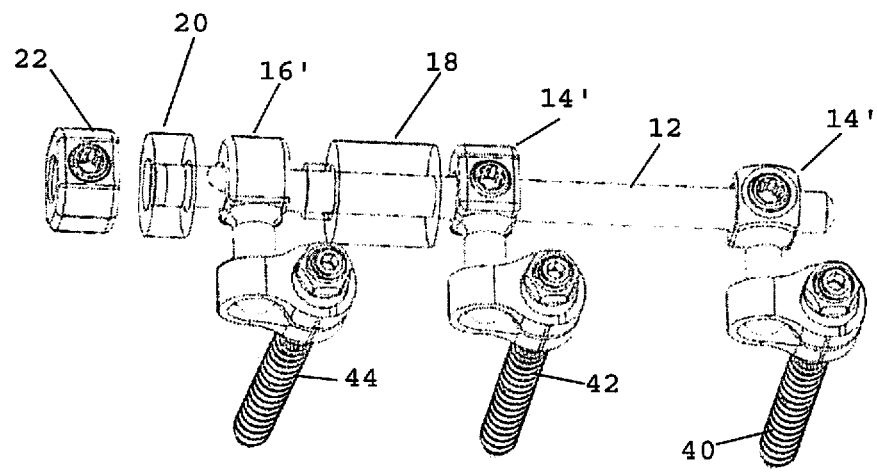
FIG. 6B is a partially exploded view of FIG. 5B.
Figure 6C:
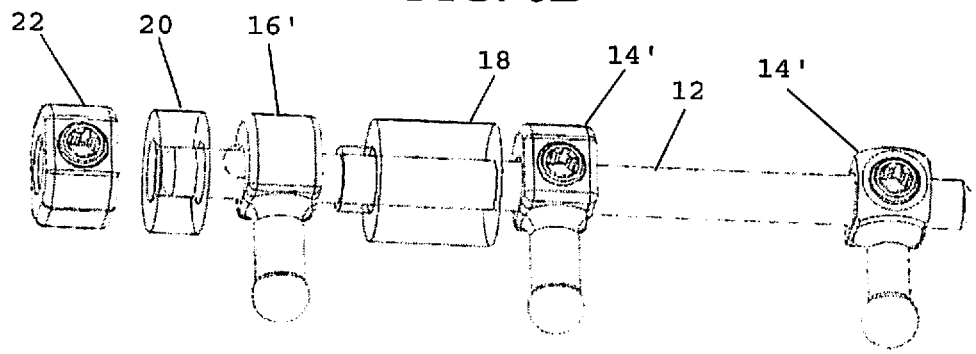
FIG. 6C is a partially exploded view of FIG. 6C.

With reference to FIGS. 5A-5C (assembled views) and FIGS. 6A-6C (partially exploded views), there is shown a system 10' configured with three pedicle screws 40, 42, and 44 and the connectors 14' and 16' that connect to the screws 40-44 are omniaxial connectors available from Choice Spine, LP of Knoxville, Tenn., and having a ball joint connection 50 to the pedicle screw.

Figure 7:
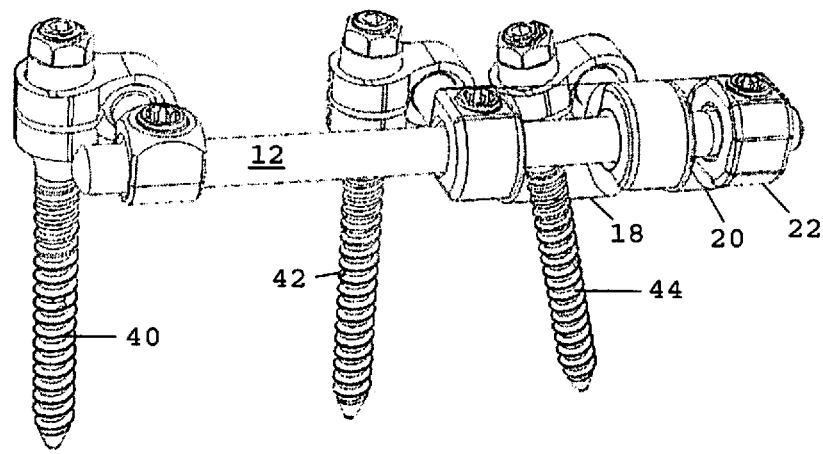
FIG. 7 shows the stabilization system of FIG. 5A in a condition of extension.
Figure 8:
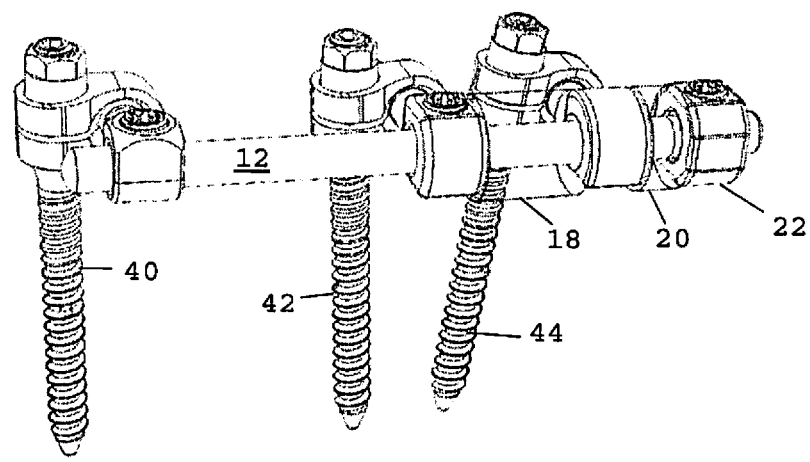
FIG. 8 shows the stabilization system of FIG. 5A in a condition of flexion.

The systems 10 and 10' enable improvement in spinal movements throughout the substantially normal range of motions from the neutral condition, to a flexion condition, and an extension condition. The systems installed with the spine positioned in the neutral condition, as shown in FIGS. 5A and 5B for the system 10', typically using pedicle screws installed in adjacent vertebrae of the spine. FIG. 7 shows the system 10' in the extension condition and FIG. 8 shows the system 10' in the flexion condition. The systems 10 and 10' are configured to eliminate metal-to-metal contact between metal components that are movable relative to one another.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A dynamic spinal stabilization system, comprising:
    a first metal pedicle screw and a second metal pedicle screw each installable in a vertebrae;
    a metal support rod;
    a first metal connector mountable to the first pedicle screw and fixedly disposed on the rod;
    a second metal connector mountable to the second pedicle screw and slidingly disposed on the rod at a location spaced apart from the first connector;
    a rigid metal member fixed to the rod and spaced apart from a side of the second connector opposite the first connector;
    a first elastomeric sleeve positioned on the rod and located between the first and second connectors, the first elastomeric sleeve having a stepped configuration and including a first section and a second section having a smaller exterior dimension than the corresponding dimension of the first section and sized to fit within a portion of the second connector so as to be situated between the second metal connector and the rod to substantially eliminate metal-to-metal contact between the second metal connector and the rod;

a second elastomeric sleeve located between the second connector and the rigid member;

wherein the sleeves are operative to substantially eliminate contact between the metal rod and the first and second metal connectors so as to substantially eliminate metal-to-metal contact of metal components of the system that are movable relative to one another, and wherein the sleeves deform to enable spinal movements throughout a range of motions from a neutral condition of the spine, to a flexion condition, and an extension condition.

2. The system of claim 1, wherein the rod is offset from the pedicle screws.

3. The system of claim 1, wherein the first and second metal connectors are omniaxial connectors.

4. The system of claim 1, further comprising a third pedicle screw and a third metal connector mountable to the third pedicle screw and disposed on the rod.

* * * * *